United States Patent
Brushwyler et al.

(10) Patent No.: US 8,657,488 B2
(45) Date of Patent: ***Feb. 25, 2014

(54) CALORIMETER

(75) Inventors: Kevin R. Brushwyler, St. Joseph, MI (US); John T. Hoss, Stevensville, MI (US); Octavio R. Latino, Berrien Springs, MI (US)

(73) Assignee: Leco Corporation, St. Joseph, MI (US)

( * ) Notice: Subject to any disclaimer, the term of this patent is extended or adjusted under 35 U.S.C. 154(b) by 1133 days.

This patent is subject to a terminal disclaimer.

(21) Appl. No.: 12/334,965

(22) Filed: Dec. 15, 2008

(65) Prior Publication Data

US 2009/0092170 A1 Apr. 9, 2009

Related U.S. Application Data

(60) Division of application No. 11/766,313, filed on Jun. 21, 2007, now Pat. No. 7,481,575, which is a continuation-in-part of application No. 11/416,970, filed on May 3, 2006, now Pat. No. 7,488,106.

(51) Int. Cl.
*G01K 17/00* (2006.01)

(52) U.S. Cl.
USPC .............................. 374/33; 374/31

(58) Field of Classification Search
USPC ..................................... 374/31, 33
See application file for complete search history.

(56) References Cited

U.S. PATENT DOCUMENTS

| | | | |
|---|---|---|---|
| 550,943 A | 12/1895 | Carpenter | |
| 931,189 A * | 8/1909 | Emerson | 374/38 |
| 1,103,915 A | 7/1914 | Junkers | |
| 1,163,367 A * | 12/1915 | Riche | 374/38 |
| 1,247,998 A | 11/1917 | Parr | |
| 2,141,453 A | 12/1938 | Schmidt | |
| 2,349,517 A | 5/1944 | Pinkerton | |
| 2,459,224 A * | 1/1949 | Hendricks | 366/274 |
| 2,982,132 A * | 5/1961 | Mendlowitz | 600/504 |
| 3,285,053 A | 11/1966 | Mazieres | |
| 3,456,490 A | 7/1969 | Stone | |
| 3,593,577 A | 7/1971 | Monner | |
| 3,599,666 A | 8/1971 | Curtis et al. | |
| 3,650,306 A | 3/1972 | Lancaster | |

(Continued)

FOREIGN PATENT DOCUMENTS

| | | |
|---|---|---|
| CH | 571218 | 12/1975 |
| DE | 238395 | 5/1910 |
| DE | 2840595 | 9/1978 |

OTHER PUBLICATIONS

US Patent Publication 2002/0013001 entitled *Process and Device for Measuring Combustion Heat in a Calorimetric Bomb*, published Jan. 31, 2002.

(Continued)

*Primary Examiner* — Mirellys Jagan
(74) *Attorney, Agent, or Firm* — Price Heneveld LLP

(57) ABSTRACT

A calorimeter includes a bucket cover which is used to reconfigure an isothermal water reservoir to provide for temperature equilibration prior to sample analysis and subsequently define a fixed volume of water during analysis in which high precision temperature measurements can be recorded. The apparatus includes mechanisms for sealing and controlling the cover, and for coupling the combustion vessel to the cover while minimizing the thermal contact between them. Improved thermal isolation between the fixed volume of water and the surrounding environment is also achieved.

7 Claims, 11 Drawing Sheets

(56) References Cited

U.S. PATENT DOCUMENTS

| | | | |
|---|---|---|---|
| 3,665,761 A | | 5/1972 | Gregory |
| 3,789,662 A | | 2/1974 | Zettler et al. |
| 3,978,325 A | | 8/1976 | Goldstein et al. |
| 4,130,016 A | * | 12/1978 | Walker ............... 374/34 |
| 4,310,162 A | | 1/1982 | Donovan |
| 4,379,775 A | | 4/1983 | Brandstetr et al. |
| 4,398,836 A | | 8/1983 | Sitek |
| 4,511,263 A | | 4/1985 | Prosen |
| 4,616,938 A | | 10/1986 | Bonnard |
| 4,670,404 A | * | 6/1987 | Swift et al. ............... 436/147 |
| 4,708,548 A | | 11/1987 | Taylor et al. |
| 4,816,730 A | | 3/1989 | Wilhelm et al. |
| 4,846,584 A | | 7/1989 | Burch et al. |
| 4,859,077 A | | 8/1989 | Ito et al. |
| 4,892,707 A | | 1/1990 | Stockton et al. |
| 4,923,306 A | | 5/1990 | Fauske |
| 4,925,315 A | | 5/1990 | Bonnard |
| 4,957,707 A | | 9/1990 | Hofelich et al. |
| 4,963,499 A | * | 10/1990 | Stockton et al. ............... 436/147 |
| 5,135,305 A | | 8/1992 | Fitz-Patrick |
| 5,322,360 A | | 6/1994 | Willis et al. |
| 5,819,508 A | | 10/1998 | Kraft et al. |
| 6,089,124 A | | 7/2000 | Murphy |
| 6,203,760 B1 | | 3/2001 | Van der Plaats et al. |
| 6,523,998 B1 | | 2/2003 | Danley et al. |
| 6,627,451 B2 | | 9/2003 | Pinhack et al. |
| 6,860,632 B2 | | 3/2005 | Groeschner |
| 6,953,280 B2 | * | 10/2005 | Fischer et al. ............... 374/33 |
| 6,991,362 B1 | * | 1/2006 | Seaman ............... 366/168.2 |
| 7,074,364 B2 | | 7/2006 | Jähn et al. |
| 7,288,229 B2 | * | 10/2007 | Turner et al. ............... 422/130 |
| 2002/0176799 A1 | | 11/2002 | McCorkle |
| 2004/0241864 A1 | | 12/2004 | Sattler et al. |
| 2009/0154520 A1 | * | 6/2009 | Richner et al. ............... 374/29 |

OTHER PUBLICATIONS

US Patent Publication 2002/0172629 entitled *Device and Method for Carrying Out Experiments in Parallel*, published Nov. 21, 2002.

US Patent Publication 2003/0043880 entitled *Method, A Measuring Cell and a System for Measuring Very Small Heat Changes in a Sample*, published Mar. 6, 2003.

Koehler Instrument K88800, www.koehlerinstrument.com/products/K88800.html, published Nov. 4, 2006.

PerkinElmer Jade Dsc literature 2006©.

U-Therm Analysis Instruments, Model JingYing, www.u-therm.net/productdetail.aspx?id=36, 2006©.

* cited by examiner

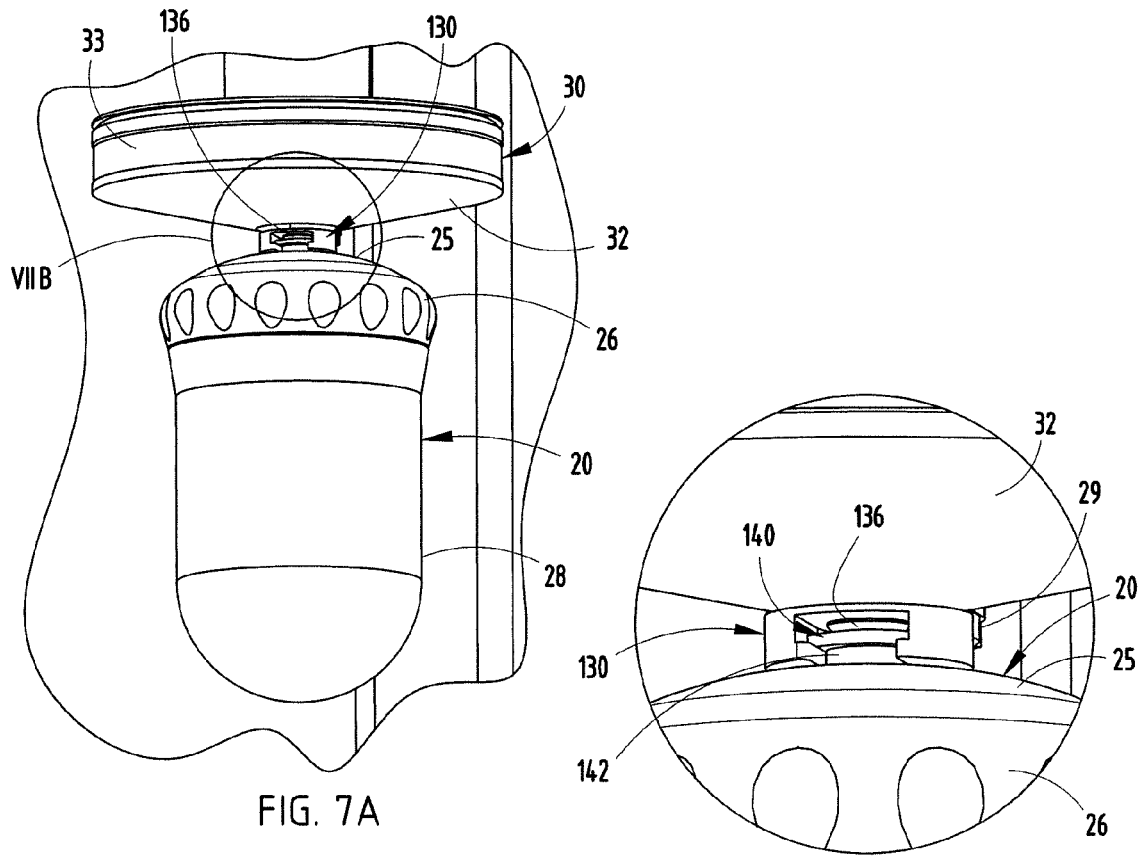
FIG. 7A
FIG. 7B
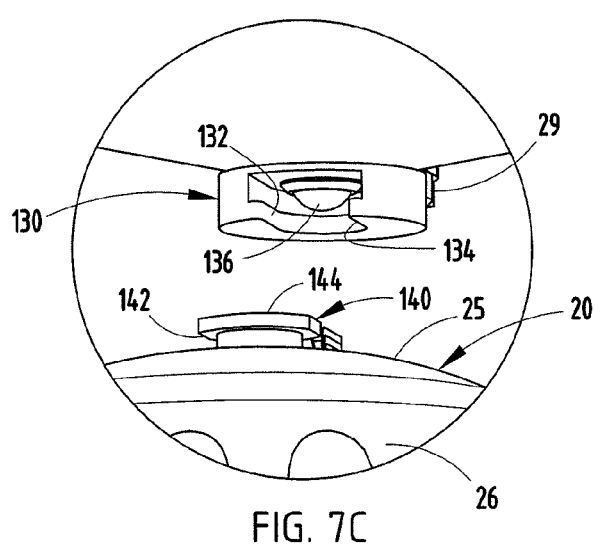
FIG. 7C

CALORIMETER

CROSS-REFERENCE TO RELATED APPLICATIONS

This application is a divisional of U.S. patent application Ser. No. 11/766,313, filed on Jun. 21, 2007 now U.S. Pat. No. 7,481,575, entitled CALORIMETER, which was a continuation-in-part of U.S. patent application Ser. No. 11/416,970 filed on May 3, 2006 now U.S. Pat. No. 7,488,106, entitled CALORIMETER, the entire disclosures of which are incorporated herein by reference.

BACKGROUND OF THE INVENTION

The present invention relates to a calorimeter including a combustion vessel and an integrated isothermal fluid reservoir.

In the past, somewhat complicated apparatus has been employed for the determination of the calorific value of solid and liquid substances in accordance with standard methodology (ASTM/ISO standards). The operation of such an apparatus is well understood and has been described in, for example, the American National Standard Institute ANSI/ASTM D5865.

Prior calorimeters have required the use of multiple internal and external reservoirs with which to contain and manage the water required to operate the apparatus. U.S. Pat. Nos. 4,398,836 and 4,616,938 disclose calorimeters which have a tank for holding a calorimeter combustion vessel and a separate water tank coupled by conduits and valves for supplying water to the vessel. In another calorimeter disclosed in U.S. Pat. No. 4,616,938, two distinct reservoirs were employed, including an internal jacket reservoir and a permanent internal bucket reservoir. In another calorimeter disclosed in U.S. Pat. No. 5,322,360, four distinct water reservoirs are employed:

1) A first internal reservoir, commonly referred to as a jacket, is employed to provide a constant isothermal environment.

2) A second internal reservoir is employed to provide a ballast volume of water from which to fill an external burette.

3) A third external reservoir, commonly referred to as a burette, is employed to deliver a reproducible amount of analysis water.

4) A fourth transportable reservoir, commonly referred to as a bucket, is used to receive the water delivered from the burette and to contain the combustion vessel. The bucket is installed in the analyzer and temperature measurements of the bucket are recorded during the course of the analysis.

One disadvantage of using separate reservoirs in a calorimeter is that, during routine operation, the systems require an external source of coolant water to eliminate thermal energy generated by the combustion of the sample. Also, the use of multiple reservoirs in such prior art systems requires numerous valves and conduits with which to direct the water to and from the reservoirs.

The operation of prior art isothermal calorimeters is further complicated by the requirement to maintain the temperature of the water substantially constant in all reservoirs from one analysis to the next. Additionally, upon the completion of an analysis, any heat resultant from the combustion of the sample must be removed.

Furthermore, prior art designs required the use of a distinctly separate bucket reservoir in order to ensure that the volume of water contained therein be maintained substantially constant from one analysis to the next. This requirement is a result of the fact that any variation in this volume is proportionally related to imprecision in the observed results. Assuming no other source of error, a variation of 1 part in 1000 in the volume of water will limit the precision of the apparatus, correspondingly, to 1 part in 1000.

Various instrument design approaches have been used to reduce this source of error. Typically, these approaches employ either a sensor or an overflow port with which to limit the volume of the water. Among other factors, such approaches are dependant either upon the surface tension of the water or the sensitivity and reproducibility of the sensor. In order to eliminate heat resultant from the combustion of the sample, these approaches require that the water in the bucket be substantially drained and refilled before each analysis. In some cases, the bucket and the combustion vessel must be dried by the operator in order to ensure that the correct volume of water is present.

SUMMARY OF THE INVENTION

In accordance with the present invention, an improved apparatus and method has been developed for determining the calorific value of combustible substances. The apparatus employs a cover, which can be used to partition a single isothermal reservoir into an outer jacket and an internal bucket for receiving the calorimeter vessel. The apparatus improves the thermal isolation between the combustion vessel and the surrounding environment to achieve more accurate results.

In one embodiment of the invention, a calorimeter system including an isothermal reservoir includes a combustion vessel; an outer jacket having a wall, a fluid inlet and an overflow outlet located near an upper end; a system for circulating fluid from said fluid inlet to provide a constant temperature of fluid within said jacket; a thermally insulated bucket positioned within said jacket in spaced relationship to the wall thereof and having an internal volume therein defining a bucket for receiving a calorimeter combustion vessel, said bucket having a height less than the height of said jacket such that fluid in said jacket fills said bucket; and a movable bucket cover coupled to said calorimeter combustion vessel and including a seal engaging said bucket for sealing said bucket from said jacket during combustion of a sample within said combustion vessel.

In another embodiment of the invention, a calorimeter including a combustion vessel and an isothermal reservoir for receiving said combustion vessel is provided and includes a lifting arm coupled to a bucket cover and to said combustion vessel for raising and lowering said combustion vessel into a bucket.

In one embodiment of the invention, the bucket cover includes an inflatable peripheral seal engaging the inner wall of the bucket to isolate the bucket from the remainder of the surrounding isothermal jacket during combustion of a sample.

In one embodiment also, the bucket cover includes a lower section with a quick disconnect coupling cooperating with the combustion vessel cover to minimize the thermal communication between the bucket cover and combustion vessel.

In order to further thermally isolate the bucket and the isothermal reservoir or jacket in one embodiment, a stirrer is included in the bucket and has two permanent magnets mounted on either side of its rotary axis which are magnetically coupled to a secondary rotary magnet drive positioned outside of the isothermal jacket to provide thermal isolation between the bucket and the jacket.

In order to raise and lower an arm holding the bucket cover and the combustion vessel, the arm is mounted to a vertically movable post which is guidably and movably supported on a vertically fixed stanchion by roller couplings. The movable post includes a support bracket which rests upon the thrust nut of a screw drive, such that the screw drive urges the movable post, bucket cover, and combustion vessel upwardly between a fully lowered immersed position to intermediate and raised positions for access to the combustion vessel. As the screw drive is reversed, the movable post lowers by gravity with the support bracket resting upon the thrust nut assembly. In the event the movable post does not follow the thrust nut in its lowering motion and the bracket and thrust nut assembly separate, a spring-loaded pawl has a locking end which engages a toothed rack on the stanchion for holding the combustion vessel supporting arm in a fixed position, thereby preventing it from uncontrollably dropping into the bucket.

These and other features, objects and advantages of the present invention will become apparent upon reading the following description thereof together with reference to the accompanying drawings.

BRIEF DESCRIPTION OF THE DRAWINGS

FIGS. 7A-7C are enlarged fragmentary perspective views of the structure coupling the combustion vessel and the bucket cover;

DETAILED DESCRIPTION OF THE PREFERRED EMBODIMENT

Figure 1:
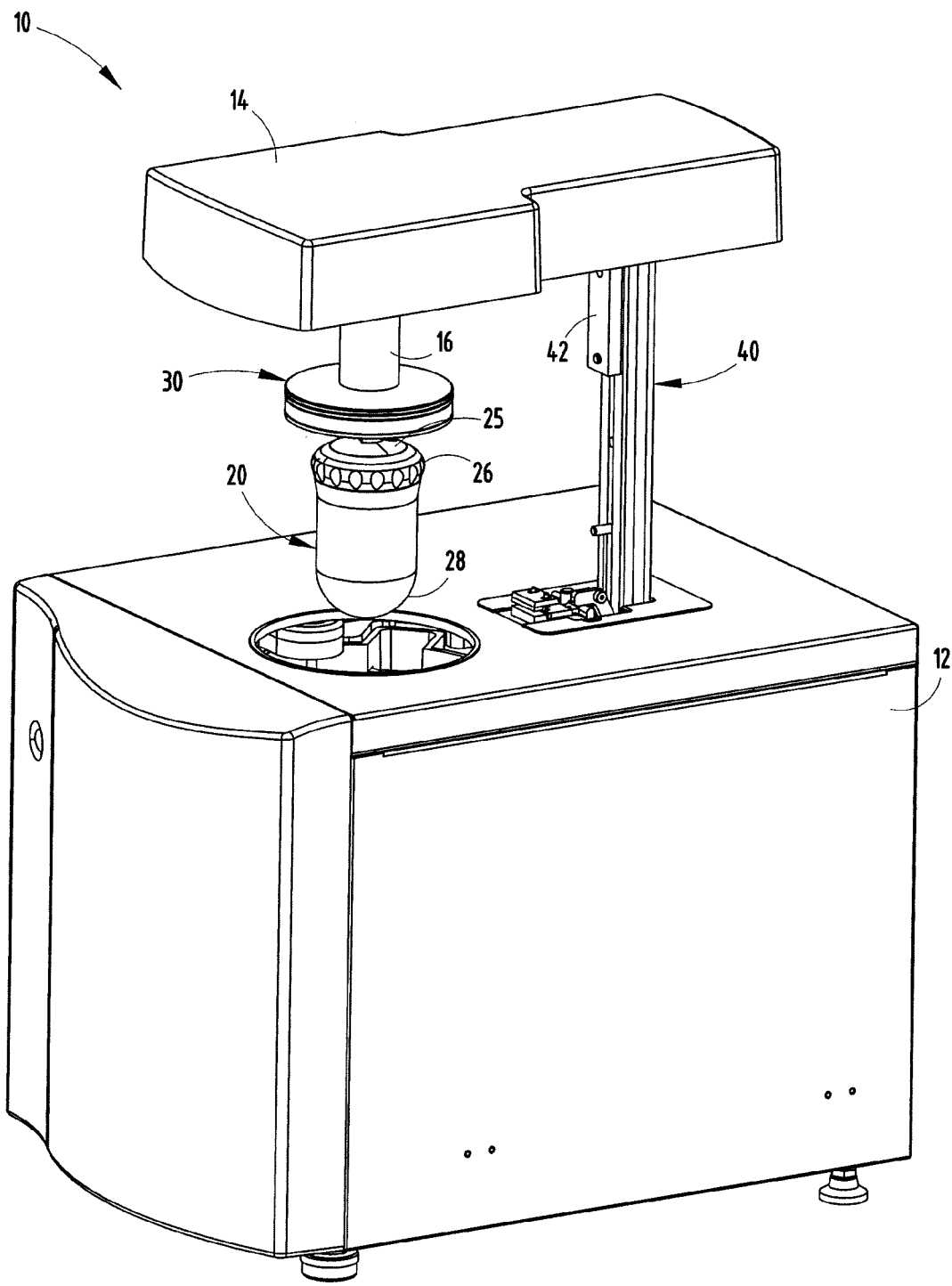
FIG. 1 is a perspective front right view of a calorimeter embodying the present invention.
Figure 2:
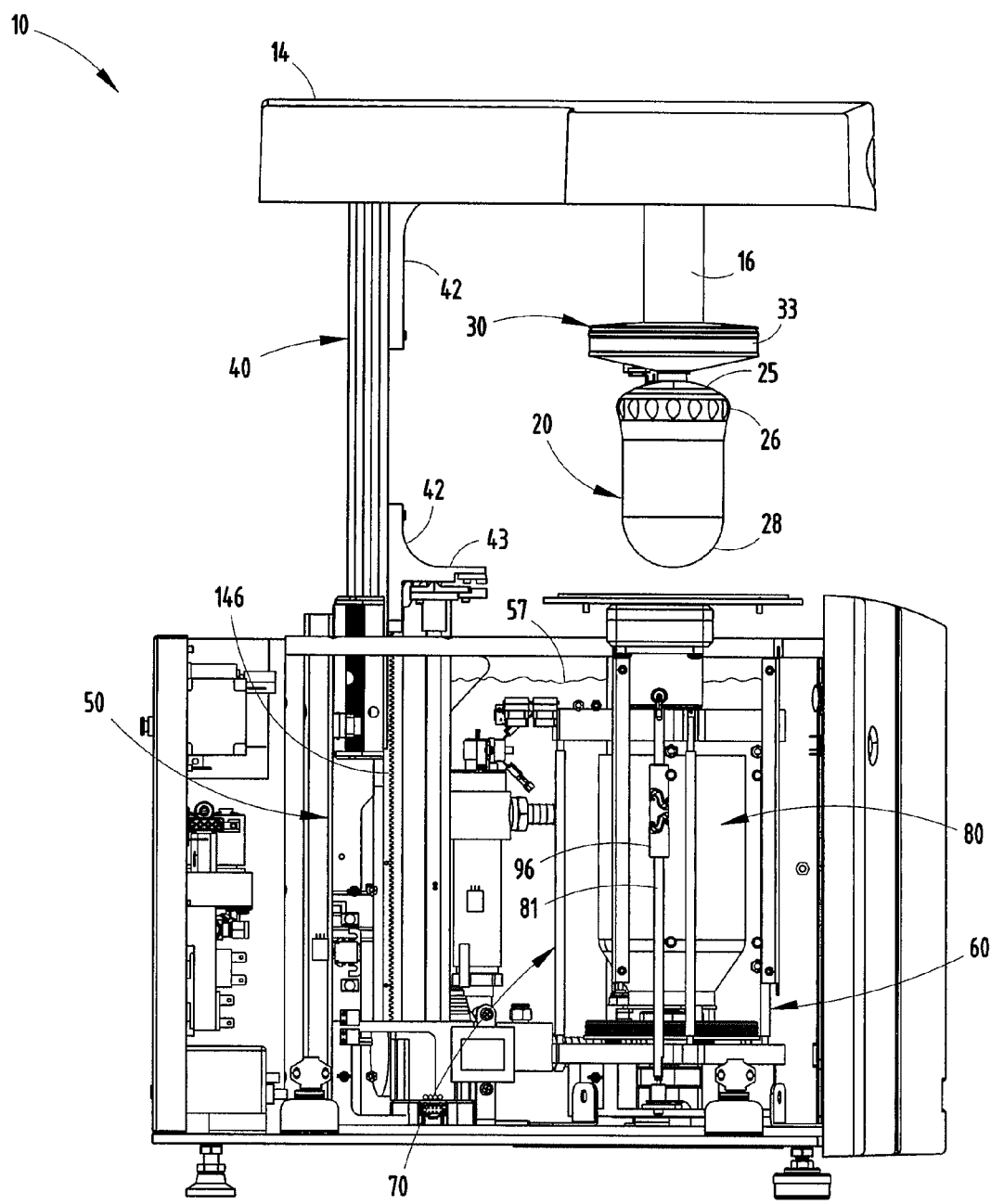
FIG. 2 is a left side elevational view, partially in vertical cross section, of the calorimeter embodying the present invention, shown with the calorimeter combustion vessel in a raised position.
Figure 3:
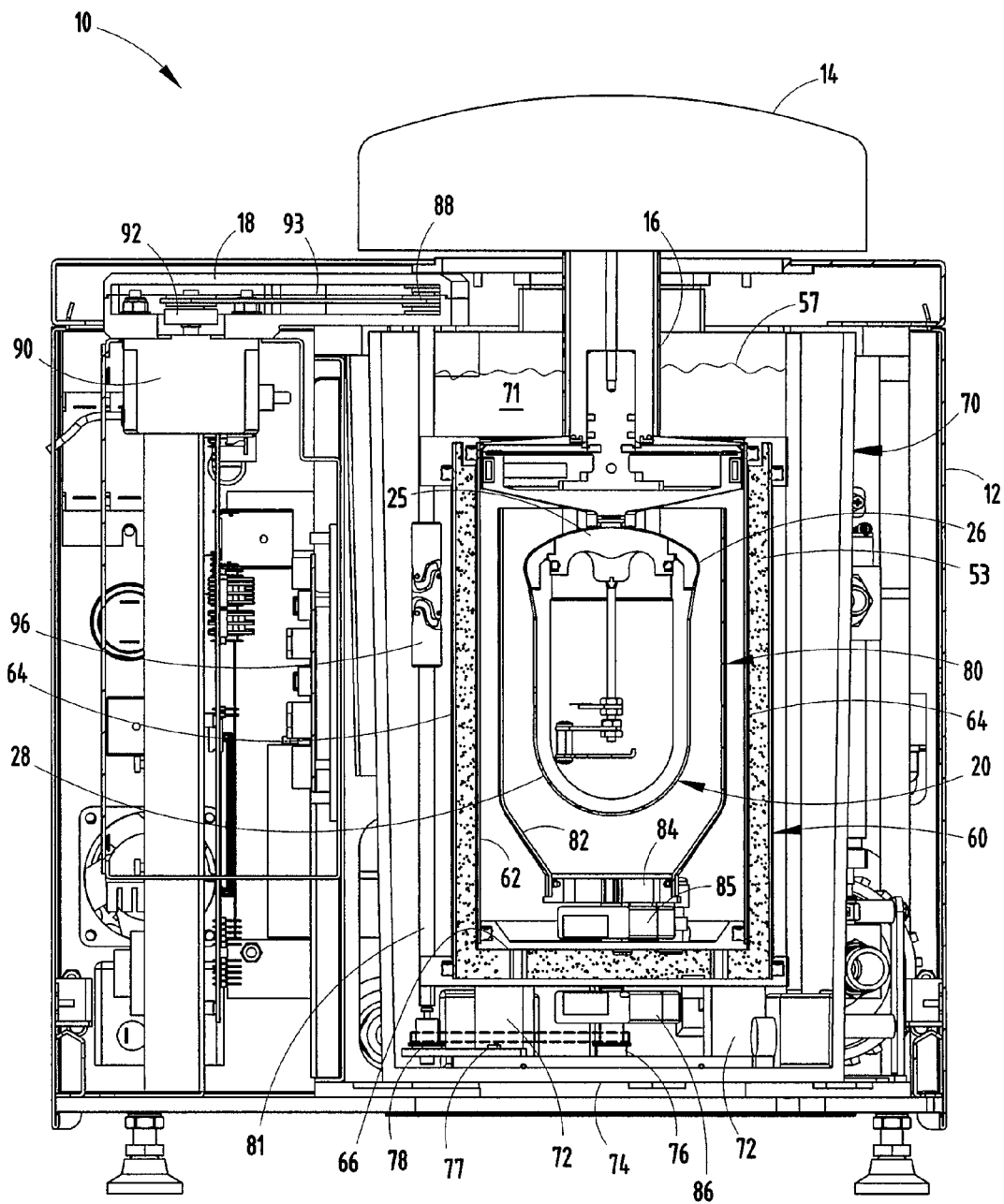
FIG. 3 is a front vertical cross-sectional view of the calorimeter embodying the present invention, shown with the calorimeter combustion vessel immersed in the bucket of the isothermal reservoir.
Figure 4:
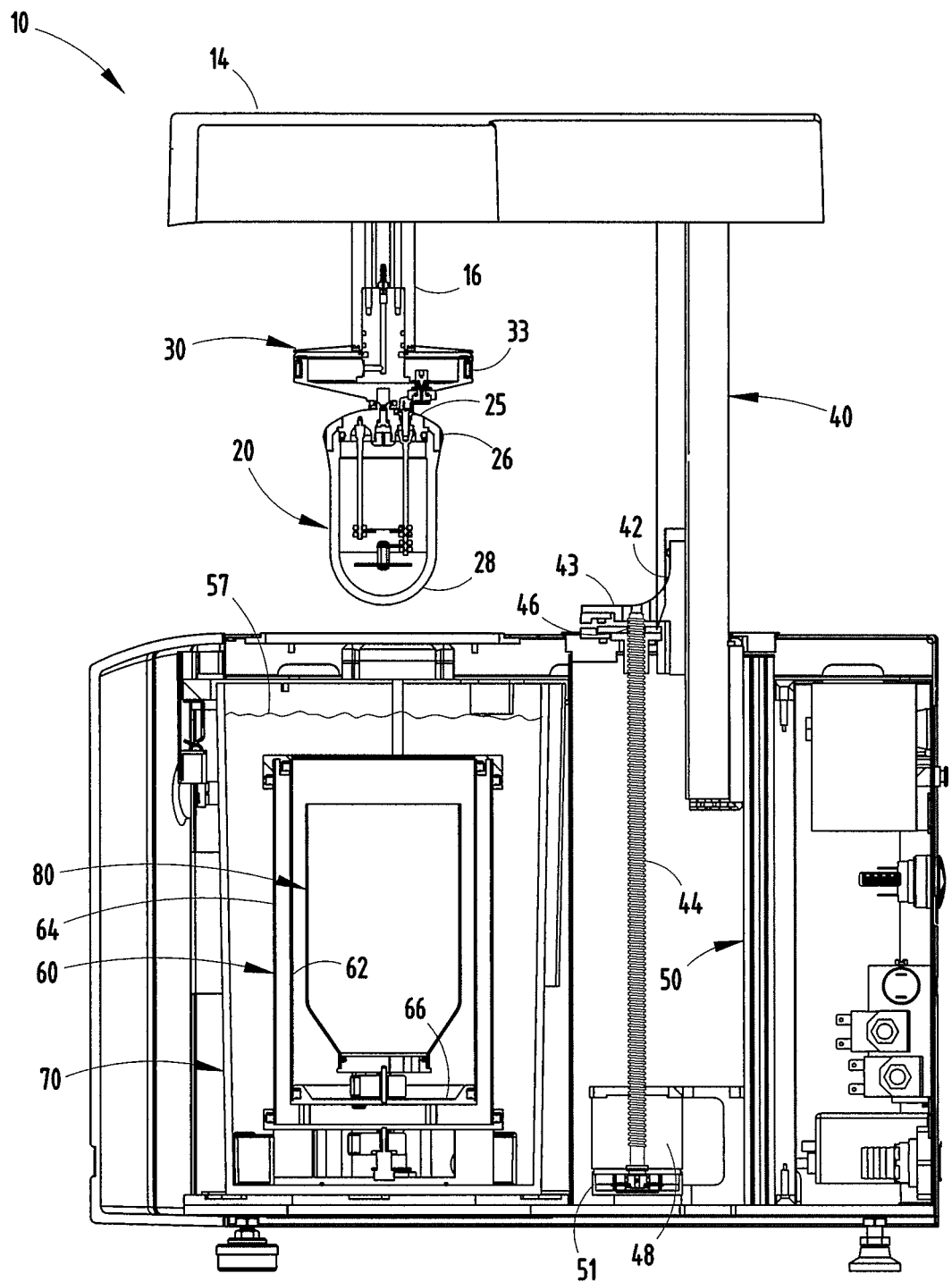
FIG. 4 is a right side elevational view in vertical cross section of the calorimeter with the calorimeter vessel raised from the isothermal reservoir.

Referring initially to FIGS. 1-4, there is shown a calorimeter 10 embodying the present invention. The calorimeter is shown in FIGS. 1, 2, and 4 in an open position for loading and removal of the combustion vessel 20 for introducing a sample, installing the ignition fuse, and filling the vessel with combustion oxygen. In FIG. 3, the calorimeter is shown in a closed position with the combustion vessel 20 immersed in an isothermal reservoir during an analysis. The calorimeter combustion vessel 20 is made of stainless steel about 0.25 inches thick with a top 25 sealably engaging the bullet-shaped curved blunt enclosed lower end 28 and is retained by a threaded closure ring 26.

Figure 8A:
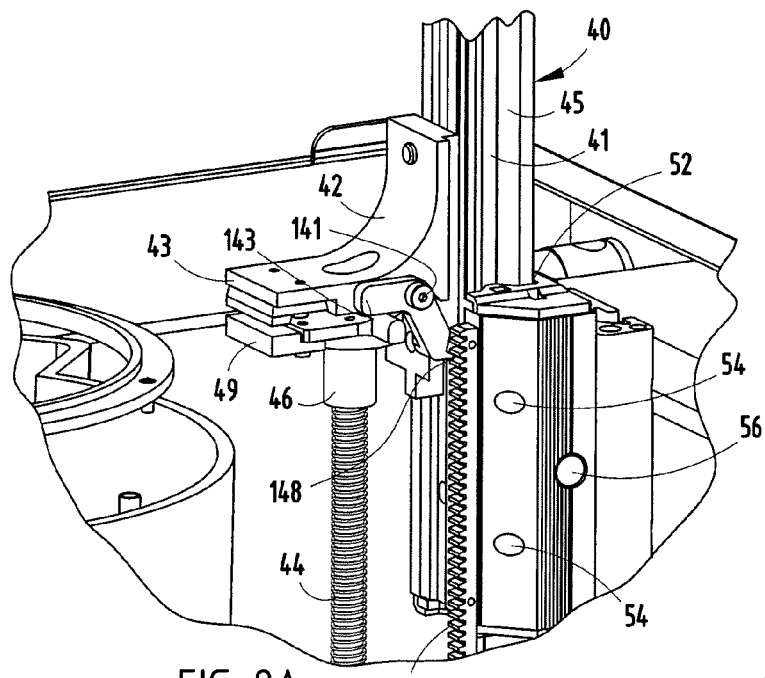
FIGS. 8A-8C are fragmentary perspective views of the raising and lowering mechanism for the calorimeter vessel.
Figure 8B:
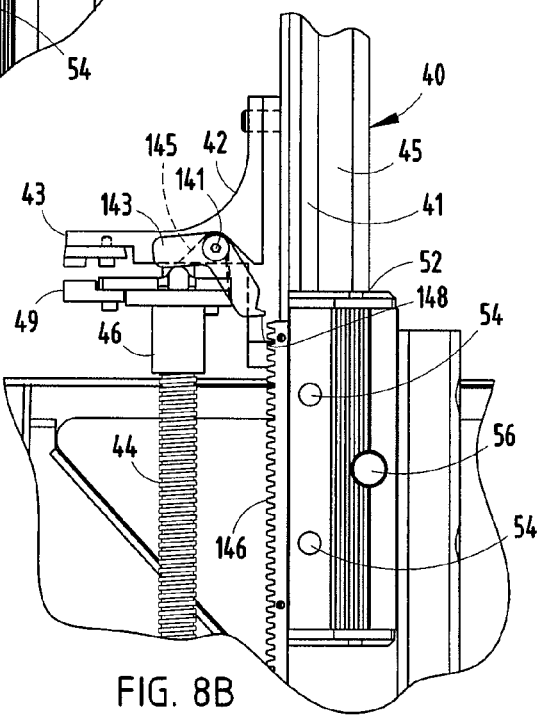
Figure 8C:
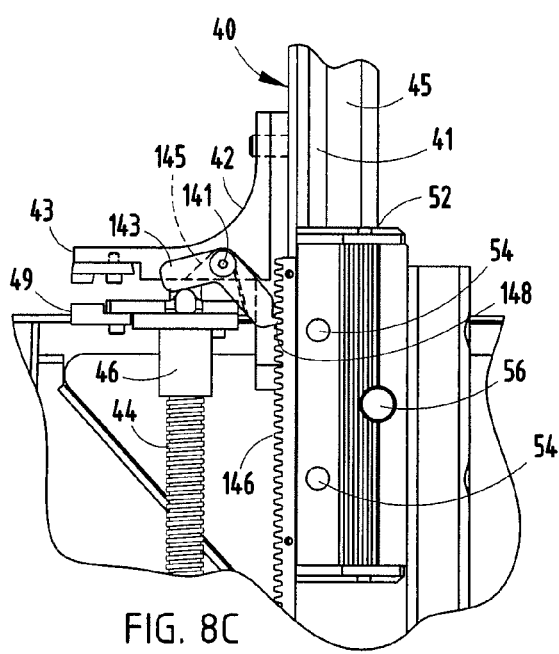
Figure 9:
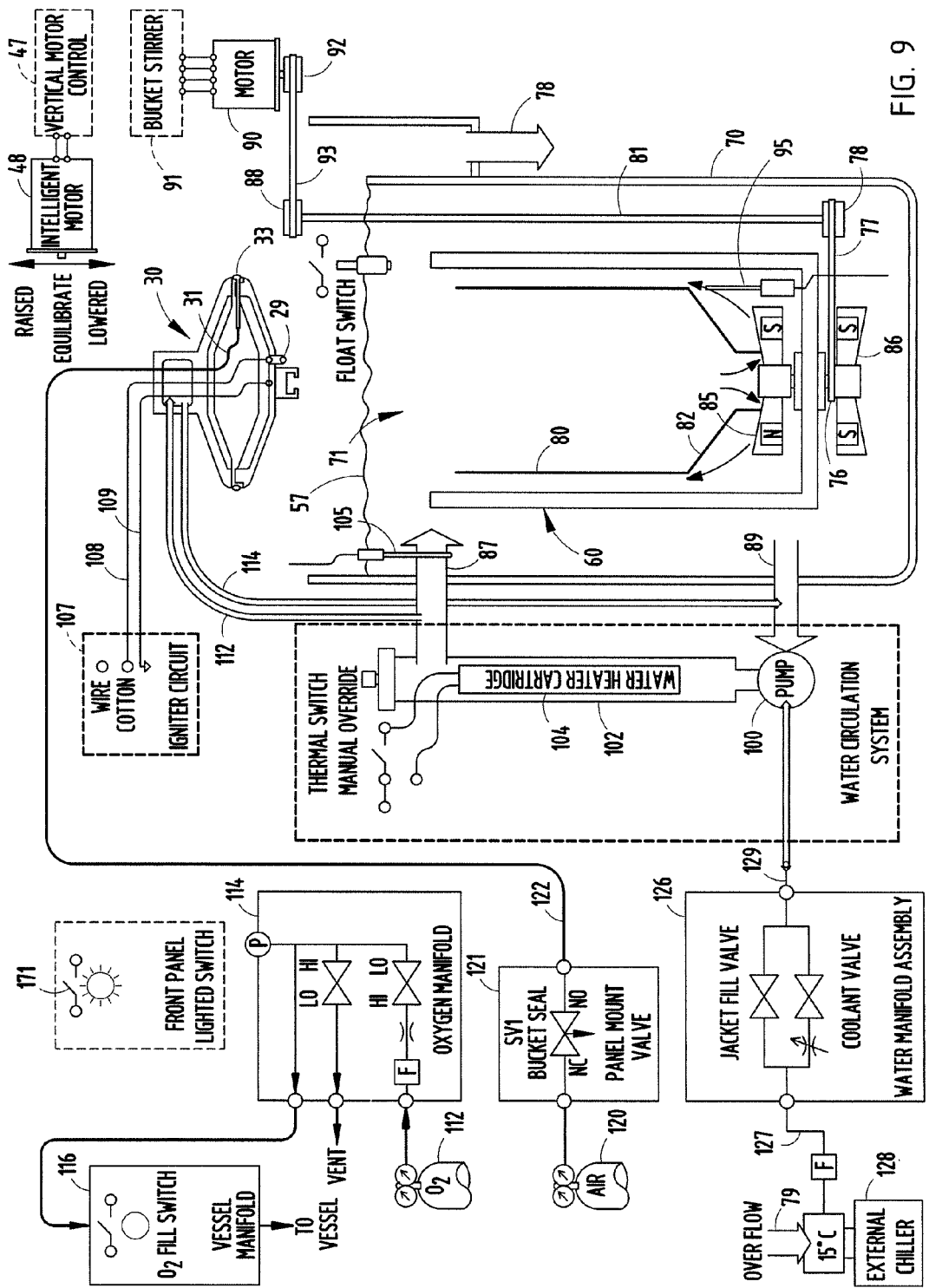
FIG. 9 is a schematic view of the calorimeter including a flow diagram of the fluid components of the calorimeter.
Figure 11:
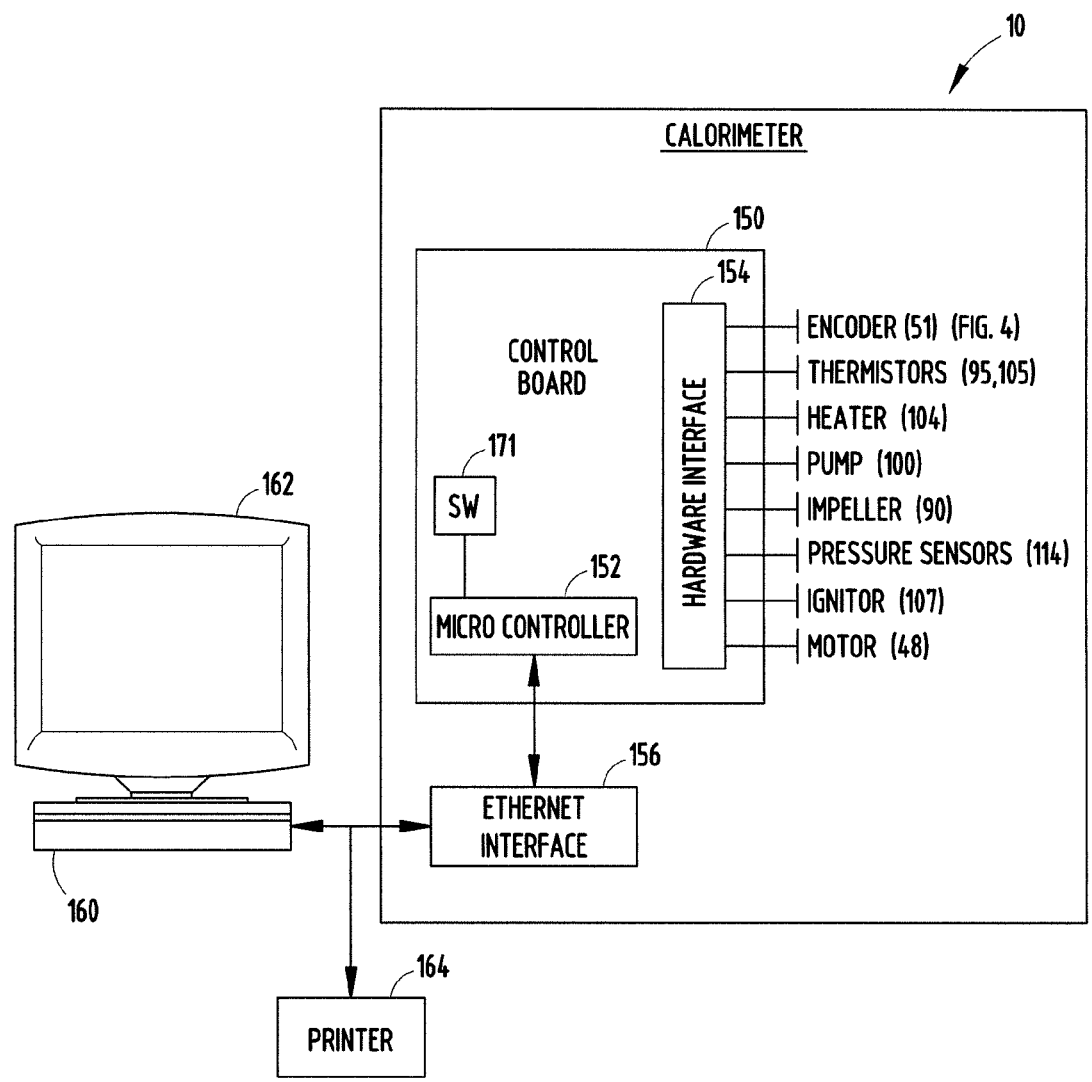
FIG. 11 is a block electrical circuit diagram of the control system for the calorimeter.

Calorimeter 10 includes a cabinet 12, as seen in FIG. 1, enclosing frame members which support the components of the calorimeter, including the fluid connections as illustrated in FIG. 9 and described below. Cabinet 12 also houses the internal components of the calorimeter as well as electrical components and coupling to an external microprocessor, display, and printer, as illustrated in FIG. 11. The combustion vessel 20 is coupled to a bucket cover 30 which, in turn, is coupled to an arm 14 by a hollow cylindrical tube 16 through which the electrical connections for firing the fuse of the combustion vessel 20 is provided, as well as a communication path for pneumatic pressure for inflating the seal associated with cover assembly 30 and water circulation, as described below. The arm 14 has internal conventional support framework for holding and coupling the arm 14 to a vertically movable post 40 which is coupled to a fixed stanchion 50 by the roller mechanism described below in FIGS. 8A-8C.

Figure 5:
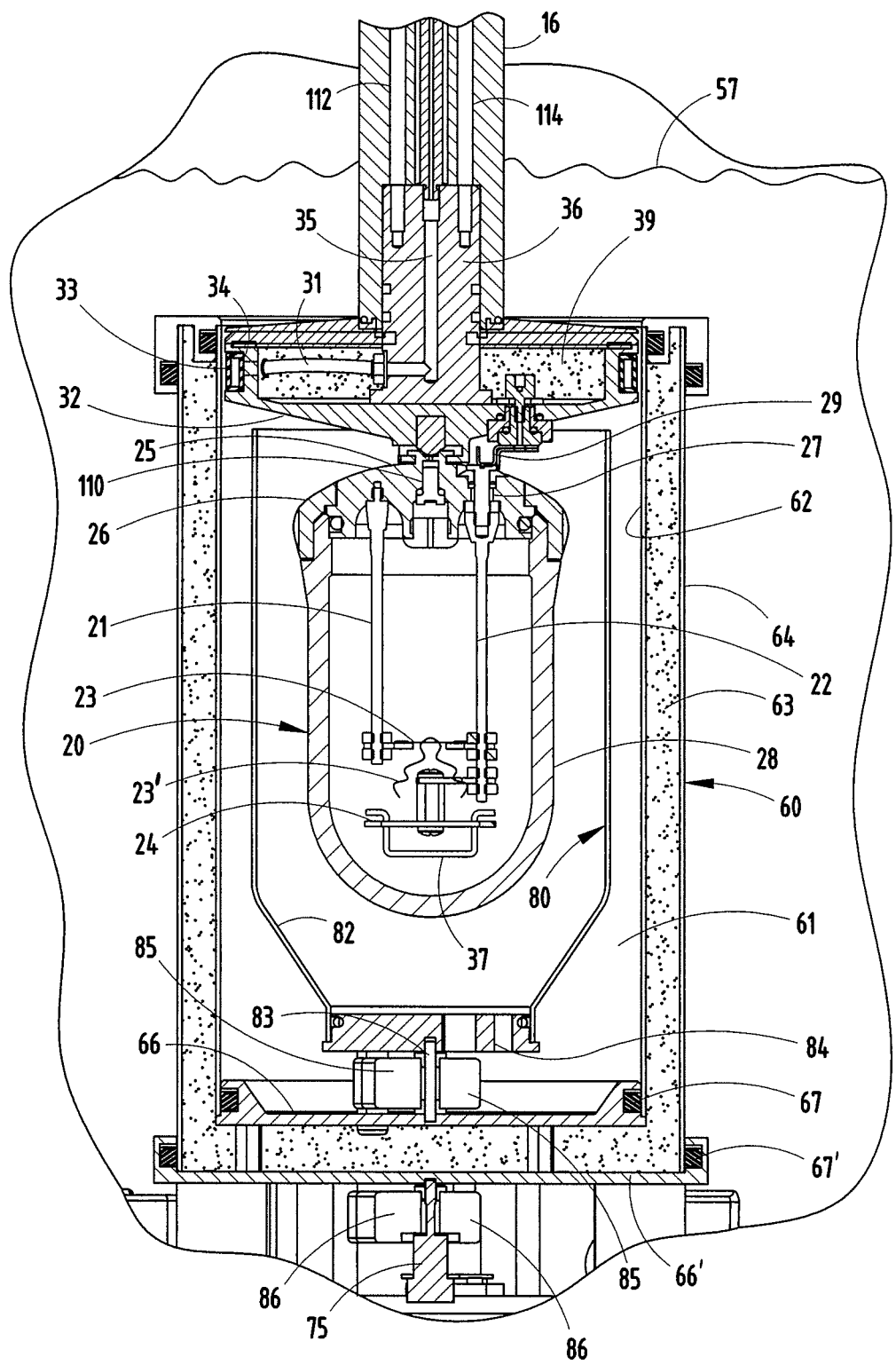
FIG. 5 is an enlarged fragmentary front vertical cross section, showing the combustion vessel immersed during an analysis, and showing the coupling of the combustion vessel to the bucket cover.

Post 40 includes a generally L-shaped support bracket 42 having a flange 43 (FIGS. 4, and 8A-8C) which rests upon a thrust nut assembly 46 driven by a threaded screw jack 44, as best seen in FIGS. 8A-8C. Screw jack 44 is rotated by a drive motor 48 to raise post 40 and the calorimeter vessel 20 coupled to arm 14 through bucket cover 30. Reversing the screw jack 44 lowers the thrust nut assembly 46 allowing the post 40 and arm 14 holding the calorimeter vessel to lower under the influence of gravity to an intermediate position, partially submerged within the isothermal bucket 60 during an intermediate step or fully immersed into the bucket 60, as shown in FIGS. 3 and 5, during an analysis. In the event the post 40 for some reason does not smoothly follow the lowering thrust nut assembly 46, the protective ratchet mechanism shown and described below in connection with FIGS. 8A-8C is employed to prevent the combustion vessel from dropping into the bucket 60.

The isothermal reservoir of the calorimeter 10 comprises an outer jacket 70 (FIGS. 3, 4, and 9) into which the isothermal bucket 60 receiving the combustion vessel 20 is mounted by thermally isolating blocks 72 (FIG. 3). Water fills the jacket 70 to a level indicated by water line 57 in the drawings. Bucket 60 includes an inner stainless steel wall 62, an outer stainless steel wall 64, and a floor 66, 66'. The space between walls 62 and 64 and floor sections 66, 66' are filled with foam insulation 63 to insulate the bucket from the surrounding isothermal reservoir defined by the interior volume 71 of jacket 70 during combustion of a sample once temperature equilibrium has been reached. Foam insulation 63 is contained between inner walls 62 and outer walls 64 of bucket 60, as best seen in FIG. 5. The floors 66, 66' are sealed to walls 62, 64 by sealing gaskets 67, 67'. The bucket 60 includes an internal baffle 80 which is generally cylindrical and has inwardly tapered lower walls 82 which are sealably coupled to an impeller 84 for circulating water around the combustion vessel 20 within bucket 60 during combustion of a sample to quickly equilibrate the water temperature within bucket 60.

Impeller 84 includes a drive shaft 83 coupled to rotating permanent magnets 85 within bucket 60. Permanent magnets 85 are magnetically coupled to permanent magnets 86 external to bucket 60 which, in turn, are rotatably mounted to the floor 74 (FIG. 3) of jacket 70 by an axle and bearing assembly 75. Magnets 86 are driven by a sprocket 76 coupled to a drive sprocket 78 by means of a drive belt 77. Sprocket 78, in turn, is driven by a vertically rotatable shaft 81 extending vertically downwardly within jacket 70 and through a flexible coupling 96 (FIG. 3), which is coupled to a drive sprocket 88 rotatably mounted to the framework within cabinet 12 by suitable bearings. Sprocket 88 is coupled to a motor 90 (FIGS. 3 and 9) by a second sprocket 92 and drive belt 93. Motor 90 is controlled by bucket motor control circuit 91 (FIG. 9).

During combustion of a specimen within combustion vessel 20 and bucket 60, impeller 84 circulates water within the bucket 60 and around baffle 80 to uniformly and quickly reach an equilibrium so that the raise in temperature as measured by the bucket thermistor 95 (FIG. 9) can be employed to determine the calorific value of the specimen being analyzed. The jacket interior 71 is supplied with circulating water through an inlet 87 and outlet 89, shown schematically in FIG. 9, coupled to a circulating pump 100 and conduit 102, which includes an electrical preheater 104 controlled to heat the water to a predetermined temperature of about 25° C. A jacket thermistor 105 is employed in connection with the control system shown in FIGS. 10 and 11 to control the jacket temperature to the desired equilibrium temperature during an analysis.

As is seen in FIG. 9, arm 14 also optionally includes water conduits 112 and 114 for providing the same temperature water as the isothermal reservoir 71 to the bucket cover 30. In addition to this unique isothermal equilibrium water supplying system to the bucket cover 30, the bucket cover 30 also has other unique features now described in connection primarily with FIGS. 5-7C.

Figure 6:
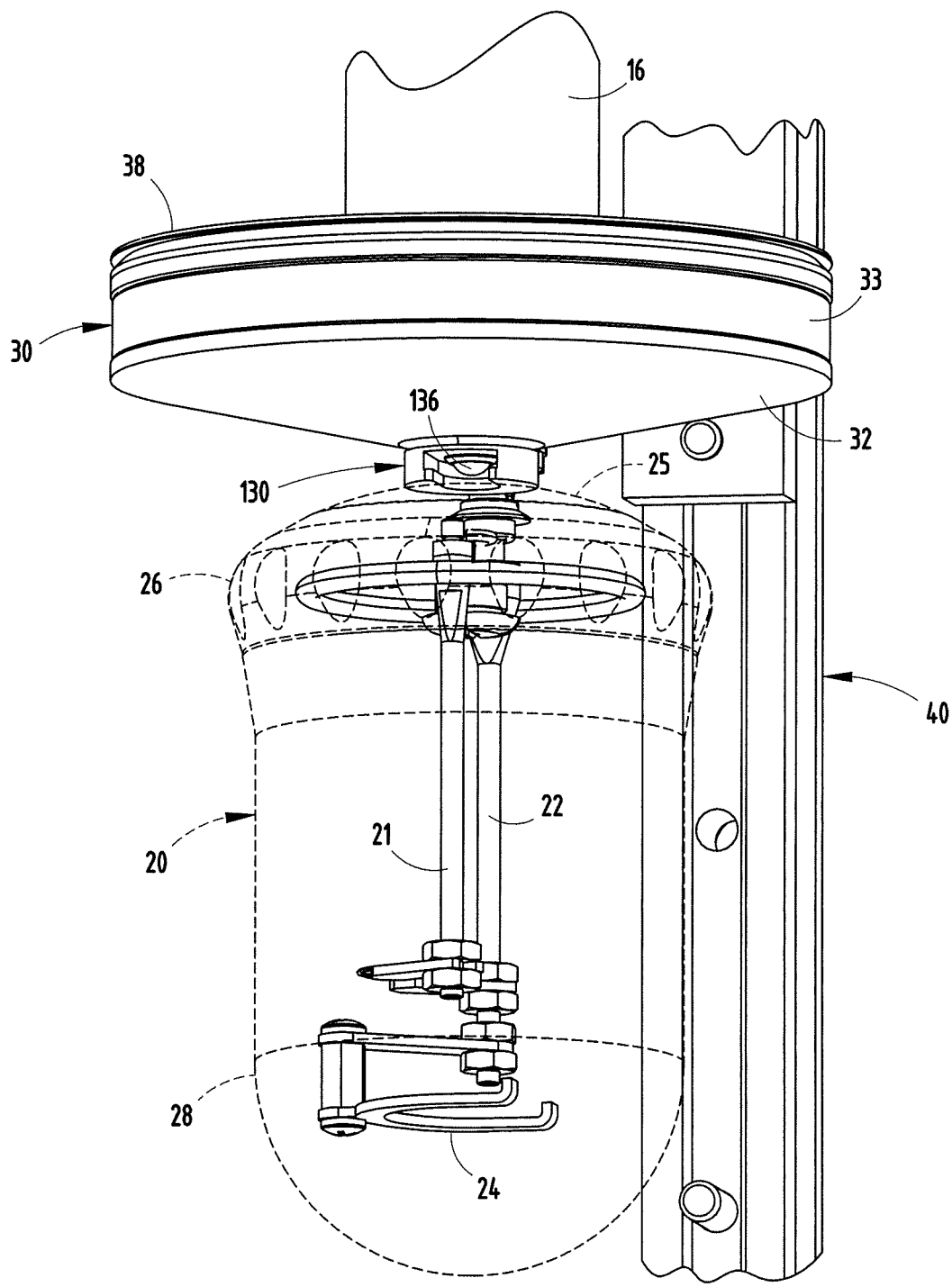
FIG. 6 is a fragmentary perspective view, partly in phantom, of the structure shown in FIG. 5, shown with the calorimeter vessel in a raised position for access.

Bucket cover 30 is shown in FIGS. 5 and 6 and comprises a generally disk-shaped body having a lower slightly tapered stainless steel member 32 which includes an annular peripheral recess 34 (FIG. 5) which holds an annular inflatable polymeric seal 33 which, when in the position shown in FIG. 5, is inflated by a pneumatic hose 31. Hose 31 extends between a passageway 35 in coupling member 36 and a suitable nipple on inflatable seal 33. Air for the seal is supplied through passageway which is coupled through tube 16 to a supply of air 120 (FIG. 9) by means of a conduit 122 and three-way valve 121. The selective operation of valve 121 selectively pressurizes the inflatable member seal 33 to seal the bucket cover 30 to the inner surface of the inner wall 62 of bucket 60 before, during, and after an analysis and exhausts the air to deflate seal 33 to allow the calorimeter vessel to be raised to the position shown in FIG. 1 for removal. Cover 30 also includes an upper closure member 38 which is sealably secured to lower member 32 by suitable fastening screws in a conventional manner. The interior space between members 38 and 32 is filled with a polymeric insulation 39 to thermally isolate the interior volume 61 of bucket 60 from jacket volume 71 during an analysis.

As seen in FIG. 5, the combustion vessel 20 includes a first electrode 21 and a second electrode 22 between which there is placed a wire filament 23 to which a cotton string 23' can be attached to initiate sample ignition. Vessel 20 also includes a valve 110 for the admission of the combustible oxygen via fill manifold 116 (FIG. 9) prior to an analysis. Combustion vessel 20 also includes a crucible-holding arm 24 (also shown in FIG. 6) for holding a crucible 37 with a specimen therein. The contact with electrode 22 is made through an insulated fitting 27 (FIG. 5) in the top 25 of vessel 20 which includes a spring contact which engages an insulated electrical spring contact 29 extending through the lower member 32 of bucket cover 30, as best seen in FIG. 5. The spring contact 29 is coupled to a firing circuit 107, which has conductors 108 and 109 (FIG. 9) which extend through tube 16 in insulated relationship within end fitting 36 in a conventional manner to provide a firing voltage through contact 29 to the fuse 23 through the positive conductor 22 within the combustion vessel 20. The igniter circuit can be selectively configured for optimum current and voltage so as to provide a means to combust either a wire fuse 23 or a cotton string 23' (FIGS. 5 and 9).

The coupling of the combustion vessel 20 to bucket cover 30 assures a minimal thermal contact between the two elements during an analysis. For such purpose, the lower member 32 of cover 30 includes, as best seen in FIGS. 7A-7C, a generally cylindrical socket 130 with a slot 132 for receiving a flanged post 140 on the cover 25 of combustion vessel 20. Post 140 includes a cylindrical neck 142 and an enlarged head 144 which fits within slot 132 and rests upon the inwardly projecting flange 134 of socket 130. Thus, the combustion vessel 20 hangs from the lower member 32 of bucket cover 30 through this detachable interconnection. To assure the interconnection remains in place during the movement of combustion vessel 20 into and out of bucket 60 and during an analysis, the socket 130 includes a spring-loaded keeper ball 136 which presses against the top surface of flange 144 to urge flange 144 into engagement with inwardly projecting flange 134 on socket 130. FIG. 7C shows the combustion vessel 20 decoupled from mounting socket 130 in cover assembly 30, while FIGS. 7A and 7B show the detail of the interconnection once the combustion vessel 20 has been mounted to the bucket cover 30. This socket and post interconnection minimizes the thermal contact between bucket cover 30 and combustion vessel 20 to provide better thermal isolation and more accurate analysis of the temperature rise of water within the inner volume 61 of bucket 60 during and analysis.

Cover 25 of combustion vessel 20 is conventionally retained by a closure ring 26 threaded either by threads or by a bayonet-thread arrangement to body 28 of the vessel. Cover 25 includes a pressure-actuated valve 110 (FIG. 5) which, as seen in FIG. 9, is employed in connection with an oxygen fill assembly including a pressurized source of oxygen 112 of approximately 450 pounds/square inch coupled through an oxygen manifold 114 to the fill manifold 116 which couples to valve 110 for filling the vessel once a sample in a crucible has been mounted within crucible-holding arm 24 and the fuse 23 positioned between electrodes 21 and 22. The filling of the vessel using elements 112-116 is substantially conventional and is employed for filling the vessel 20 prior to an analysis. Subsequent to an analysis, the gas pressure inside the vessel is released by manually depressing valve 110.

The isothermal jacket volume 71 is initially filled from a source of water through a manifold assembly 126 (FIG. 9), which receives water at a temperature of approximately 15° C. controlled from a supply of water 127 with an external chiller 128 in the event the water temperature is too high. The manifold assembly 126 is coupled to a check valve 129 to the pump 100 which serves to fill the jacket 70 and circulate water through the jacket. Jacket 70 includes an overflow discharge 78 which is coupled to the input 79 of the external chiller 128 in a recirculation loop as seen in FIG. 9. Bucket cover 30 and the vessel 20 coupled thereto is moved between a raised position shown in FIGS. 1 and 2 to a lowered operating position for an analysis, as shown in FIGS. 3 and 5, by drive motor 48 shown in FIGS. 4 and 9. The interconnection of the movable post 40 to fixed stanchion 50 to achieve this motion is now described in connection with FIGS. 8A-8C.

Drive motor 48 is actuated by a motor control 47 (FIG. 9). The motor 48, as shown in FIG. 4, drives the threaded jack screw 44 coupled to the thrust nut 46, which raises the bracket 42 fixed to movable post 40. Post 40 is coupled to the stanchion 50 by means of channel 52 within stanchion 50 which receives the configured side extensions 41 of post 40 in smoothly movable relationship. Side rollers 54 are vertically spaced along both sides of extensions 41 and ride within channel 45 defined therebetween. Front and rear rollers 56 provide stability in the fore and aft direction for post 40. The thrust nut 46 is mounted to a plate 49 which engages the lower surface of bracket 42 and, as screw jack 44 is rotated in a first direction, plate 49 raises, thereby lifting bracket 42 and post 40 attached thereto to the fully raised position shown in FIGS. 1 and 4. A shaft encoder 51 (FIG. 4) is coupled to circuit 47 and determines the number of revolutions of jack screw 44 and thereby provides the system information as to the vertical position of combustion vessel 20 during its movement between the raised position, a substantially submerged position (not shown), and the fully submerged position (FIGS. 3 and 5).

There is no locked mechanical connection between plate 49 and bracket 42 other than the physical contact as plate 49 is raised by thrust nut 46. When the arm 14 holding vessel 20 and attached to post 40 is lowered by reversing the direction of the jack screw 44, a flange 43 on bracket 42 rests upon the upper surface of plate 49 and follows plate 49 as it is lowered. As long as plates 49 and flange 43 are in contact, a spring-loaded pawl 143, which is mounted to bracket 42, is in a non-locking position with respect to a geared, toothed rack 146. Pawl 143 is pivotally mounted by a pin 141 to bracket 42 and has a locking end 148 which engages notches 147 in rack 146 in the event flange 43 and plate 49 become separated. If post 40 smoothly follows the lowering of plate 49, pawl 143 is held in a non-locked position by the contact of plate 49 and flange 43 against pawl 143 compressing spring 145. If these plates become separated as shown in FIG. 8C, spring 145 rotates the locking end 148 of pawl 143 which engages the rack 146, thereby holding the arm 14 and combustion vessel 20 in a fixed vertical position until the operator can manually lower the arm 14 by releasing pawl 143 against the spring bias 145 while holding the arm against rapid acceleration downwardly. This interconnection between the jack screw 44 and post 40 allows for relatively quiet operation of the raising and lowering of combustion vessel 20 and provides a safety feature preventing inadvertent rapid lowering of the combustion vessel.

Figure 10:
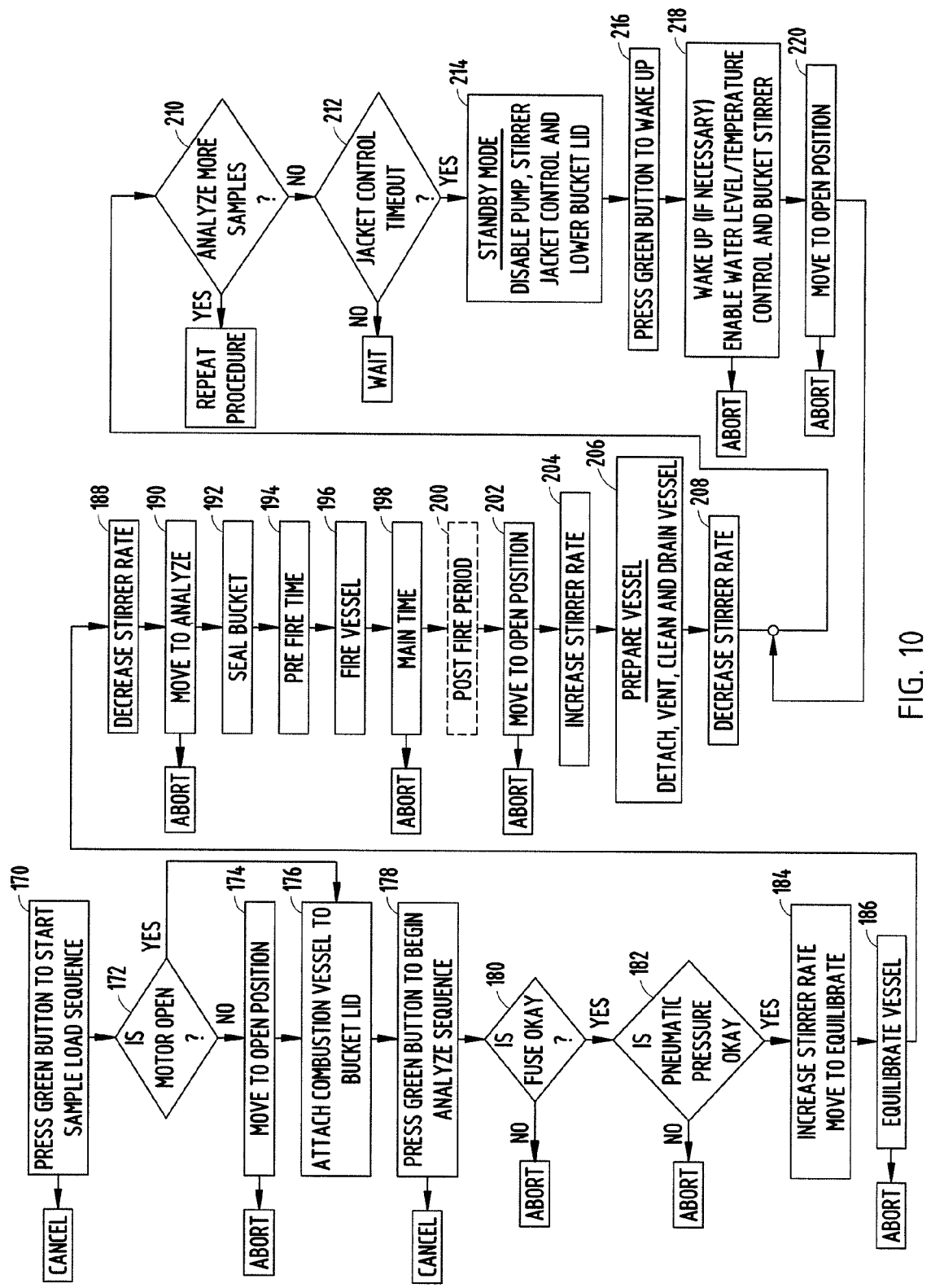
FIG. 10 is a flow diagram showing the steps in the sequence of operation of the calorimeter of the present invention.

The sequence of operation of a cycle of an analysis is shown in connection with the flow diagram of FIG. 10 in which the various motors and temperature sensors shown in FIG. 9 are employed in connection with the microcontroller 152 contained on the control board 150 (FIG. 11). As seen in FIG. 10, the sequence of an analysis is initiated by the actuation of the start switch 171 (FIGS. 9 and 10) in which position of motor 48 as determined by the shaft encoder 51 is detected. If the combustion vessel and arm 14 are not in the raised open position as shown in FIGS. 1 and 2 as indicated by test 172, the microcontroller 152 actuates motor 48, as indicated by block 174, to the raised open position. At that time, the precharged and loaded combustion vessel 20 is attached to socket 130 of lower member 32 of bucket cover 30 by means of post 140, as illustrated in FIGS. 7A-7C and lower the combustion vessel so as to equilibrate thermally with the jacket water, as partially shown by block 176. Switch 171 is then again actuated to begin the analysis sequence, as shown by block 178. The microcontroller tests the fuse 23 (FIG. 5) for continuity, as indicated by block 180 and tests the pneumatic pressure from source 120, as shown by block 182. Next, as indicated by block 184, motor 90 is actuated to increase the stirring rate of impeller 84 through the drive shaft 81 and the temperature of water in the jacket volume 71 is measured by thermistor 105 (FIG. 9) to determine if the isothermal reservoir defined thereby has reached an equilibrium temperature of about 25° C. As it approaches the equilibrium temperature, the stirring rate is decreased, as indicated by block 188, and motor 48 is actuated to lower combustion vessel 20 into the bucket 60, as indicated by block 190. Next, the inflatable seal 133 (FIGS. 5 and 9) is inflated by the actuation of valve 121 to seal the bucket 60 from the surrounding reservoir 71, as indicated by block 192.

A timer delays firing, as indicated by block 194, until equilibrium temperature has been reached upon sealing of the bucket and, as indicated by block 196, the fuse is then fired to combust the oxygen within vessel 20 and the sample contained by the crucible contained therein. The temperature signals from thermistor 95 are then monitored, as indicated by blocks 198 and 200, utilizing a standard thermographic methodology to determine the calorific value of the combusted sample due to the increase in water temperature upon combustion of the sample. Subsequently, seal 33 is deflated by the opening of three-way valve 121 and motor 48 is actuated to raise the combustion vessel from the bucket 60, as indicated by block 202. The stirring rate is then increased, as indicated by block 204 through motor 90 to again equilibrate the overall isothermal reservoir 71 with the now increased bucket water temperature in preparation for subsequent analysis. As necessary, cold water from the external chiller 128 is allowed to flow into the jacket so as to refill and cool the jacket water.

As indicated by block 206, the vessel 20 is then detached, vented, cleaned, drained, rinsed, and the rate of stirrer 85 is decreased, as indicated by block 208, as equilibrium temperature is reached between the water in bucket 60 and jacket volume 71. If additional samples are to be run, as indicated by test 210, the procedure beginning at block 170 is repeated. If not, as indicated by block 212, the jacket temperature can be reduced to a standby mode, as indicated by block 214, to disable the pump 100, the stirrer 90, the jacket temperature control 104, and the bucket cover 30 is lowered to enclose the calorimeter in a position indicated in FIG. 5 without the addition of the combustion vessel 20. A new analysis can begin at a later time, as indicated in block 216, by actuation of switch 171 (FIG. 9), which initiates the control 104, as indicated by block 218. As indicated by block 220, cover 30 is moved to an open position for access for mounting a combustion vessel 20 thereto. Then, the test for block 210 is run to determine whether or not the sequence returns to block 170 for operation of the calorimeter.

The control elements are shown in FIG. 11 coupled to the microcontroller 152 by an interface circuit 154, with the microcontroller 152 being coupled to the personal computer 160 by means of Ethernet interface 156. Computer 160 conventionally includes a monitor 162 which displays the sequence of operation corresponding to the steps shown in the diagram of FIG. 10 and is also coupled to a printer 164 such that a printout of the results of an analysis can be obtained.

Thus with the calorimeter of this invention, improved thermal isolation between the calorimeter bucket and its surrounding components is provided. Also the sealing of the bucket cover to the bucket is improved as is its coupling to the combustion vessel. A quiet and reliable and yet inexpensive drive system is provided for raising and lowering the combustion vessel into the bucket is also provided.

It will become apparent to those skilled in the art that various modifications to the preferred embodiments of the invention as described herein can be made without departing from the spirit or scope of the invention as defined by the appended claims.

The invention claimed is:

1. A calorimeter system including an isothermal reservoir comprising:
   a calorimeter combustion vessel;
   an outer jacket having a wall, a fluid inlet and a fluid outlet;

a heater and a pump associated with said jacket for circulating fluid from said fluid outlet through said heater to said inlet to provide a constant temperature of fluid within said jacket;

a thermally insulated bucket positioned within said jacket and having an internal volume for receiving said calorimeter combustion vessel, said bucket having a height less than the height of said jacket such that fluid in said jacket fills said bucket; and a movable cover selectively coupled to said calorimeter combustion vessel and including a seal engaging said bucket for sealing said bucket from said jacket during combustion of a sample within said combustion vessel.

2. The system as defined in claim 1 wherein said bucket includes a baffle and a floor having an impeller for circulating fluid around said combustion vessel within said bucket on opposite sides of said baffle for homogenizing the temperature of the fluid contained within said bucket.

3. The system as defined in claim 1 wherein said jacket includes upper fluid inlets coupled to a discharge end of said pump, wherein one inlet is directed toward said jacket volume surrounding said thermally insulated bucket and another inlet is directed to the area above an upper end of said bucket to introduce fluid into said bucket for quickly homogenizing the fluid temperature within said bucket and jacket.

4. The system as defined in claim 1 wherein said bucket comprises a generally cylindrical member and said cover engages said bucket to seal said bucket when said combustion vessel is lowered into said bucket.

5. The system as defined in claim 4 wherein said bucket includes a baffle and a floor having an impeller for circulating fluid around said combustion vessel within said bucket on opposite sides of said baffle for homogenizing the temperature of the fluid contained within said bucket, and wherein said impeller includes magnetic poles mounted therein and wherein said jacket further includes a rotating permanent magnet for rotating said impeller.

6. The system as defined in claim 5 wherein said jacket includes a temperature detecting member and wherein said system further includes a control circuit coupled to said temperature detecting member and to said heater for controlling the temperature of the fluid within said jacket and said bucket.

7. The system as defined in claim 6 wherein said system further includes a measurement temperature sensor positioned within said bucket for detecting the temperature of the fluid surrounding said combustion vessel prior to and after combustion of a sample.

\* \* \* \* \*